US012447044B2

(12) United States Patent
Wang

(10) Patent No.: US 12,447,044 B2
(45) Date of Patent: Oct. 21, 2025

(54) MULTI-FUNCTIONAL PHYSIOTHERAPEUTIC SHOE AND TROUSER ASSEMBLY

(71) Applicant: Zhenguo Wang, Jiangsu (CN)

(72) Inventor: Zhenguo Wang, Jiangsu (CN)

( * ) Notice: Subject to any disclaimer, the term of this patent is extended or adjusted under 35 U.S.C. 154(b) by 449 days.

(21) Appl. No.: 17/993,970

(22) Filed: Nov. 24, 2022

(65) Prior Publication Data

US 2023/0085951 A1 Mar. 23, 2023

Related U.S. Application Data

(63) Continuation-in-part of application No. PCT/CN2021/000084, filed on Apr. 12, 2021.

(30) Foreign Application Priority Data

May 29, 2020 (CN) ......................... 202010498062.5

(51) Int. Cl.
*A61F 7/00* (2006.01)
*A61H 23/02* (2006.01)

(52) U.S. Cl.
CPC ............ *A61F 7/007* (2013.01); *A61H 23/02* (2013.01); *A61F 2007/0043* (2013.01); *A61F 2007/0045* (2013.01); *A61F 2007/0071* (2013.01)

(58) Field of Classification Search
CPC ...... A61F 2007/0039; A61F 2007/0041; A61F 2007/0043; A61F 2007/0045; A61F 2007/0071; A61F 2007/0249; A61F 7/007; A61H 2201/0207; A61H 2201/10; A61H 2201/1207; A61H 2205/106; A61H 2205/12; A61H 23/02; A61H 36/00
See application file for complete search history.

(56) References Cited

U.S. PATENT DOCUMENTS

2020/0155342 A1* 5/2020 Schultz .............. B65D 81/3888
2021/0338413 A1* 11/2021 Haluska ............. A61H 23/0254

FOREIGN PATENT DOCUMENTS

| | | | | |
|---|---|---|---|---|
| CN | 2882671 | Y | * | 3/2007 |
| CN | 202077587 | U | | 12/2011 |
| CN | 202859425 | U | | 4/2013 |
| CN | 203060280 | U | | 7/2013 |
| CN | 103653320 | A | | 3/2014 |
| CN | 205626245 | U | | 10/2016 |
| CN | 206995473 | U | | 2/2018 |
| CN | 208625969 | U | | 3/2019 |
| CN | 209171480 | U | | 7/2019 |
| CN | 111658290 | A | | 9/2020 |

OTHER PUBLICATIONS

International search report of PCT/CN2021/000084.

* cited by examiner

*Primary Examiner* — Tigist S Demie

(57) ABSTRACT

A multi-functional physiotherapeutic shoe and trouser assembly belongs to domestic health-care physiotherapeutic devices, and is characterized in that a shoe-shaped heating cover and rollable heating wraps with vibrators made of thermal conductive silicone can perform hot compress and massage physiotherapy on the foot, ankle, lower leg and thigh, so as to realize the functions of disease treatment and health care. The product is convenient to use and portable, can be used in bed, and improves the conditions of home care for patients, thus having better efficacy.

1 Claim, 2 Drawing Sheets

MULTI-FUNCTIONAL PHYSIOTHERAPEUTIC SHOE AND TROUSER ASSEMBLY

CROSS REFERENCE TO RELATED APPLICATIONS

The present application is a continuation-application of International (PCT) Patent Application No. PCT/CN2021/000084, filed on Apr. 14, 2021, which claims the priority of the Chinese patent application No. 202010498062.5, filed on May 29, 2020, and the entire contents of which are hereby incorporated by reference in their entireties.

TECHNICAL FIELD

The present invention belongs to domestic health-care physiotherapeutic devices.

BACKGROUND

The health care function of foot physiotherapy is well known, but there are only two types of pedicure devices on the market at present: soaking type pedicure devices which use water as a medium for heat conduction, and non-contact pedicure devices which use a space heat source for close-range radiation. The two types of pedicure devices have limited functions, and due to the restriction of structure, they can only generate a physiotherapeutic effect on the part below the knee. Moreover, users have to sit with feet hanging down, so for people who are ill abed, those with leg injuries or disabilities, and those who are unable to move freely due to age, the above-mentioned devices are inconvenient to use or even unusable.

SUMMARY

A multi-functional physiotherapeutic shoe and trouser assembly comprises a shoe-shaped heating cover, a lower leg heating wrap with a first electric vibrator and a thigh heating wrap with a second electric vibrator. A shoe cover body of the shoe-shaped heating cover is made of thermal conductive silicone, and provided with an electrothermal resistor inside, such that inner surfaces of an upper and a bottom of the shoe cover body can generate heat uniformly. An outer surface of the shoe cover body can be covered with a thermal insulation protective layer. A wrap body of the lower leg heating wrap with the first electric vibrator is made of thermal conductive silicone, can be rolled into a trouser leg shape due to the flexibility and wrapped around a lower leg of a user, and is provided with an electrothermal resistor inside to realize uniform heat generation of an inner surface; an outer surface can be covered with a thermal insulation protective layer; and the first electric vibrator is installed at a position, corresponding to leg muscles, of the wrap body of the lower leg heating wrap. A wrap body of the thigh heating wrap with the second electric vibrator is made of thermal conductive silicone, can be rolled into a trouser leg shape due to the flexibility and wrapped around a thigh of the user, and is provided with an electrothermal resistor inside to realize uniform heat generation of an inner surface; an outer surface can be covered with a thermal insulation protective layer; and the second electric vibrator is installed at a position, corresponding to leg muscles, of the wrap body of the thigh heating wrap. In this way, hot compress physiotherapy can be performed on surfaces of a foot, the lower leg and the thigh simultaneously or separately, and vibration massage physiotherapy can be performed on the lower leg and the thigh simultaneously or separately, so as to realize functions of disease treatment and health care. These components are described separately as follows:

The functions and characteristics of the invention are as follows.

1. This product can treat the whole lower limb at the same time, or treat each part separately, and can be used in a sitting posture or a sleeping posture. The trouser part is of a segmented wrapping type, which is easy to put on and take off, and can be used separately. By adding a leg massage function, hot compress and massage are combined to dredge channels and promote blood circulation, improve physiological condition, relieve muscle spasm, treat functional degeneration, and help lose weight healthily. Moreover, the conditions of home care are improved for patients, and efficacy is improved.

2. Compared with soaking type pedicure devices, since this product can perform hot compress on the whole lower limb, users with leg and foot injuries for whom soaking is not suitable can still get physiotherapy treatment; compared with the non-contact pedicure devices, this product has a much better heat transfer effect, temperature is easier to control, and a massage function is added; compared with a simple hot compress physiotherapeutic belt, this product realizes hot compress of feet; compared with a simple massage device, this product realizes simultaneous or alternate hot compress and massage, and has effects which cannot be realized by these two physiotherapies; and compared with a point type acupoint physiotherapeutic device, this product adopts a surface heat source which can transfer heat to the human body to improve the physiological state, so the curative effect is better than that of a point heat source physiotherapeutic device which only stimulates acupoints.

3. Different from wearable thermal devices without a heat source, this product has a heat source, so the physiotherapeutic effect is better; and for other wearable thermal devices with a heat source which adopt cotton or wool as the material of the part in contact with the skin, though the warming effect is realized, sweat cannot be transferred out in time, and the heat transfer efficiency cannot meet the requirements of physiotherapy.

DETAILED DESCRIPTION

Figure 1:
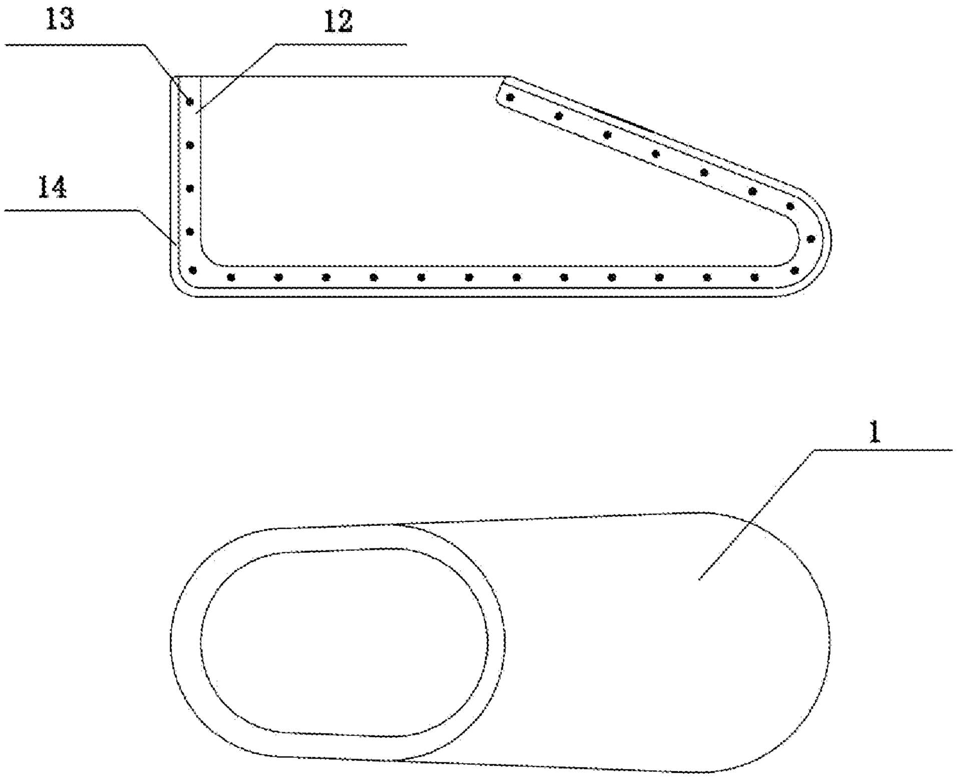
FIG. 1: Shoe-shaped heating cover

A multi-functional physiotherapeutic shoe and trouser assembly comprises a shoe-shaped heating cover 1, a lower leg heating wrap 2 with a first electric vibrator 4 and a thigh heating wrap 3 with a second electric vibrator 5.

1. Shoe-shaped heating cover 1 (see attached FIG. 1): A shoe cover body 12 is made of thermal conductive silicone, with an electrothermal resistor 13 inside and a thermal insulation protective layer 14 outside. Inner surfaces of an upper and a bottom of the shoe cover body can generate heat uniformly, so as to heat the surface of the foot. Surfaces of the upper and the bottom of the shoe cover body 12 in contact with the skin can be smooth surfaces, or can be provided with point type or line type bosses or grooves, the bosses can be formed by paving or inlaying other thermal conductive materials, and a plurality of air holes are distributed in the grooves to facilitate sweat transfer of the skin surface, thus improving the comfort level. The shoe cover body can be partially split and tightened with elastic bands or buckles.

Figure 2:
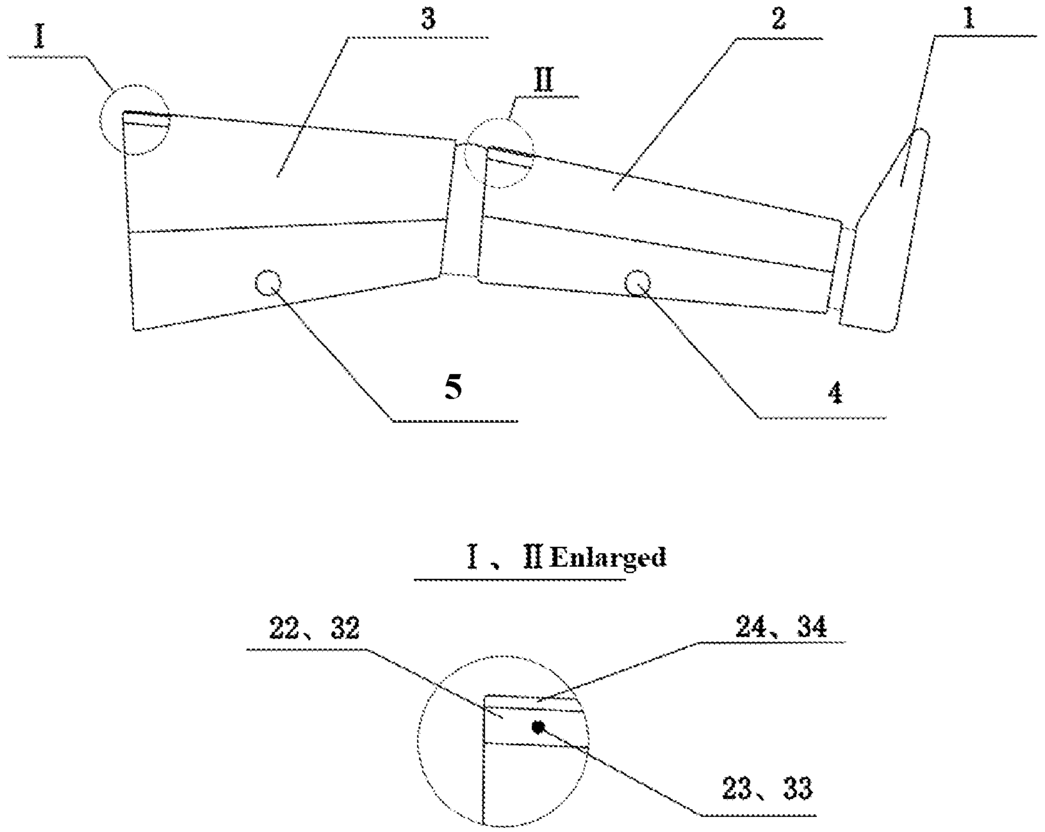
FIG. 2: Hot compress physiotherapeutic trouser with vibrator.

2. Lower leg heating wrap 2 with a first electric vibrator 4 and a thigh heating wrap 3 with a vibrator 5 (see attached FIG. 2): A wrap body 22 and a wrap body 32 are both made of thermal conductive silicone and provided with an electrothermal resistor 23 and an electrothermal resistor 33 respectively, and can be rolled into a trouser leg shape due to the flexibility and wrapped around the lower leg and thigh of a user respectively. Inner surfaces of the wrap body 22 and the wrap body 32 can generate heat uniformly, and outer surfaces are provided with a thermal insulation protective layer 24 and a thermal insulation protective layer 34 respectively. The first electric vibrator 4 and the second electric vibrator 5 are installed at positions corresponding to leg muscles. In this way, vibration massage can be performed on the thigh and the lower leg separately while hot compress is performed on the foot and leg or when hot compress is stopped. A multi-part splicing type structure can be adopted to adapt to the change of the cross section of the leg, end joints can recede according to the shape characteristics and bending degrees of the foot and knee joint, inner surfaces in contact with the skin can be smooth surfaces, or can be provided with point type or line type bosses or grooves, the bosses can be formed by paving or inlaying other thermal conductive materials, and a plurality of air holes are distributed in the grooves to facilitate sweat transfer of the skin surface. Hot compress and vibration massage physiotherapy can be performed on the leg simultaneously or separately. Here, the heating wrap is called physiotherapeutic trouser, which is based on conventional terms people use for articles worn on the legs, and is also for the convenience of description.

3. Power supply, temperature and vibrator frequency controllers obtain safe voltage and display, adjust and control heating temperature and vibrator frequency.

The silicone production technology is mature currently, and the technology of using thermal conductive silicone and electrothermal resistors to produce rollable and flexible surface heaters is also mature. Therefore, a shoe-shaped heating cover and a rollable heating wrap can also be produced. In order to better adapt to different figures, large, medium and small sizes can be provided, and splitting, sectioning or elastic band transition can also be adopted to improve adaptability. An outer layer can be covered with a cotton or leather protective layer and hemmed to prolong the service life. Vibrator frequency can be divided into strong, medium and weak grades, and stepless frequency conversion can also be adopted. Power supply and temperature sensing and control, and vibrator frequency adjustment and control are easy to realize because of the mature existing technology. Because silicone is an insulator and does not absorb water, electric leakage caused by sweat and moisture will not occur.

What is claimed is:

1. A multi-functional physiotherapeutic shoe and trouser assembly, consisting of a shoe-shaped heating cover (1), a lower leg heating wrap (2) with a first electric vibrator (4) and a thigh heating wrap (3) with a second electric vibrator (5), wherein a shoe cover body (12) of the shoe-shaped heating cover (1) is made of thermal conductive silicone, and provided with an electrothermal resistor (13) inside, such that inner surfaces of an upper and a bottom of the shoe cover body (12) generate heat uniformly;

an outer surface of the shoe cover body (12) is covered with a thermal insulation protective layer (14);

a wrap body (22) of the lower leg heating wrap (2) with the first electric vibrator (4) is made of thermal conductive silicone, is able to be rolled into a trouser leg shape due to its flexibility and wrapped around a lower leg of a user, and is provided with an electrothermal resistor (23) inside to realize uniform heat generation on an inner surface; an outer surface is covered with a thermal insulation protective layer (24); and the first electric vibrator (4) is installed at a position, corresponding to leg muscles, of the wrap body (22) of the lower leg heating wrap (2);

a wrap body (32) of the thigh heating wrap (3) with the second electric vibrator (5) is made of thermal conductive silicone, is able to be rolled into a trouser leg shape due to its flexibility and wrapped around a thigh of the user, and is provided with an electrothermal resistor (33) inside to realize uniform heat generation on an inner surface; an outer surface is covered with a thermal insulation protective layer (34); and the second electric vibrator (5) is installed at a position, corresponding to leg muscles, of the wrap body (32) of the thigh heating wrap (3); and in this way, hot compress physiotherapy is able to be performed on surfaces of a foot, the lower leg and the thigh simultaneously or separately, and vibration massage physiotherapy is able to be performed on the lower leg and the thigh simultaneously or separately, so as to realize functions of disease treatment and health care.

* * * * *